(12) United States Patent
Niemeyer, III et al.

(10) Patent No.: US 9,433,423 B2
(45) Date of Patent: Sep. 6, 2016

(54) ADJUSTABLE RATCHETING VASCULAR COMPRESSION DEVICE AND METHOD OF USE

(71) Applicants: Robert Henry Niemeyer, III, Tigard, OR (US); Philip Benz, Portland, OR (US); Matthew Semler, Portland, OR (US)

(72) Inventors: Robert Henry Niemeyer, III, Tigard, OR (US); Philip Benz, Portland, OR (US); Matthew Semler, Portland, OR (US)

(73) Assignee: Semler Technologies, Inc., Milwaukie, OR (US)

( * ) Notice: Subject to any disclaimer, the term of this patent is extended or adjusted under 35 U.S.C. 154(b) by 233 days.

(21) Appl. No.: 14/227,160

(22) Filed: Mar. 27, 2014

(65) Prior Publication Data

US 2015/0272592 A1    Oct. 1, 2015

(51) Int. Cl.
*A61B 17/132* (2006.01)
(52) U.S. Cl.
CPC ....... *A61B 17/1327* (2013.01); *A61B 17/1325* (2013.01)
(58) Field of Classification Search
CPC .......... A61B 17/1327; A61B 17/1322; A61B 17/132; A61B 17/1325; Y10T 24/141; Y10T 24/1406; B65D 63/1063; B65D 63/1081; B65D 63/1027
See application file for complete search history.

(56) References Cited

U.S. PATENT DOCUMENTS

| | | | | |
|---|---|---|---|---|
| 4,897,899 A | * | 2/1990 | Shely | B65D 63/1072 24/16 PB |
| 5,269,803 A | * | 12/1993 | Geary | A61B 17/1322 606/201 |
| 2012/0053617 A1 | * | 3/2012 | Benz | A61B 17/1325 606/203 |
| 2014/0082923 A1 | * | 3/2014 | Owen | F16L 3/233 29/525.03 |

* cited by examiner

*Primary Examiner* — Thomas McEvoy

(57) ABSTRACT

A ratcheting adjustable vascular compression device assists in achieving partial or full occlusion of a blood vessel when applied to a patient's limb, during or following a medical procedure. During deployment, a compression pad on the device applies preferential compression to at least one portion of the circumference of the limb. Further, securement, adjustment and rapid release of the device are all enabled by an alternate ratcheting mechanism that enables gradual adjustments to be made to the tightness and thus to the compression applied without releasing the device, so as to permit patent blood flow through blood vessels in the limb during the compression period.

10 Claims, 10 Drawing Sheets

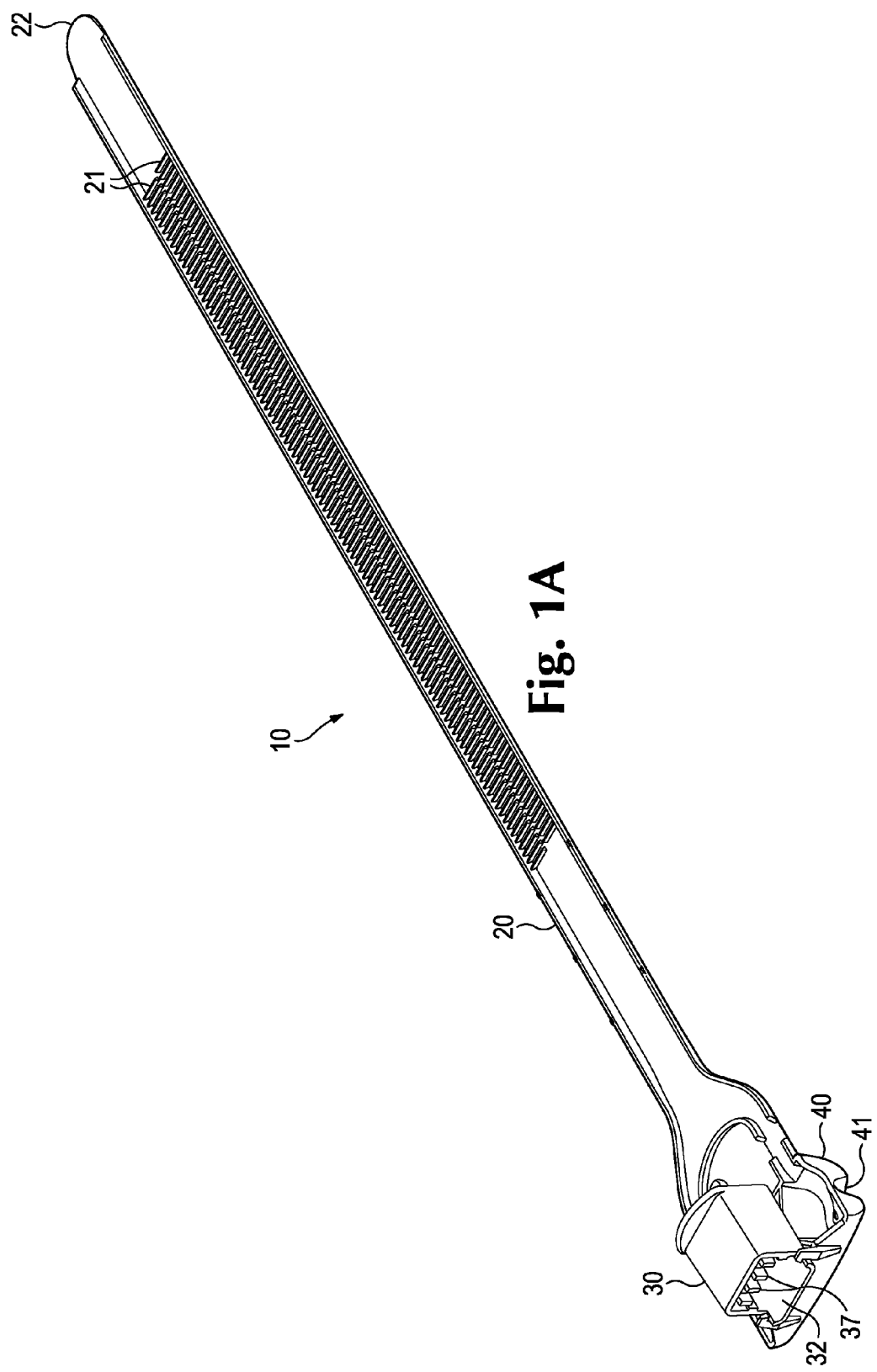

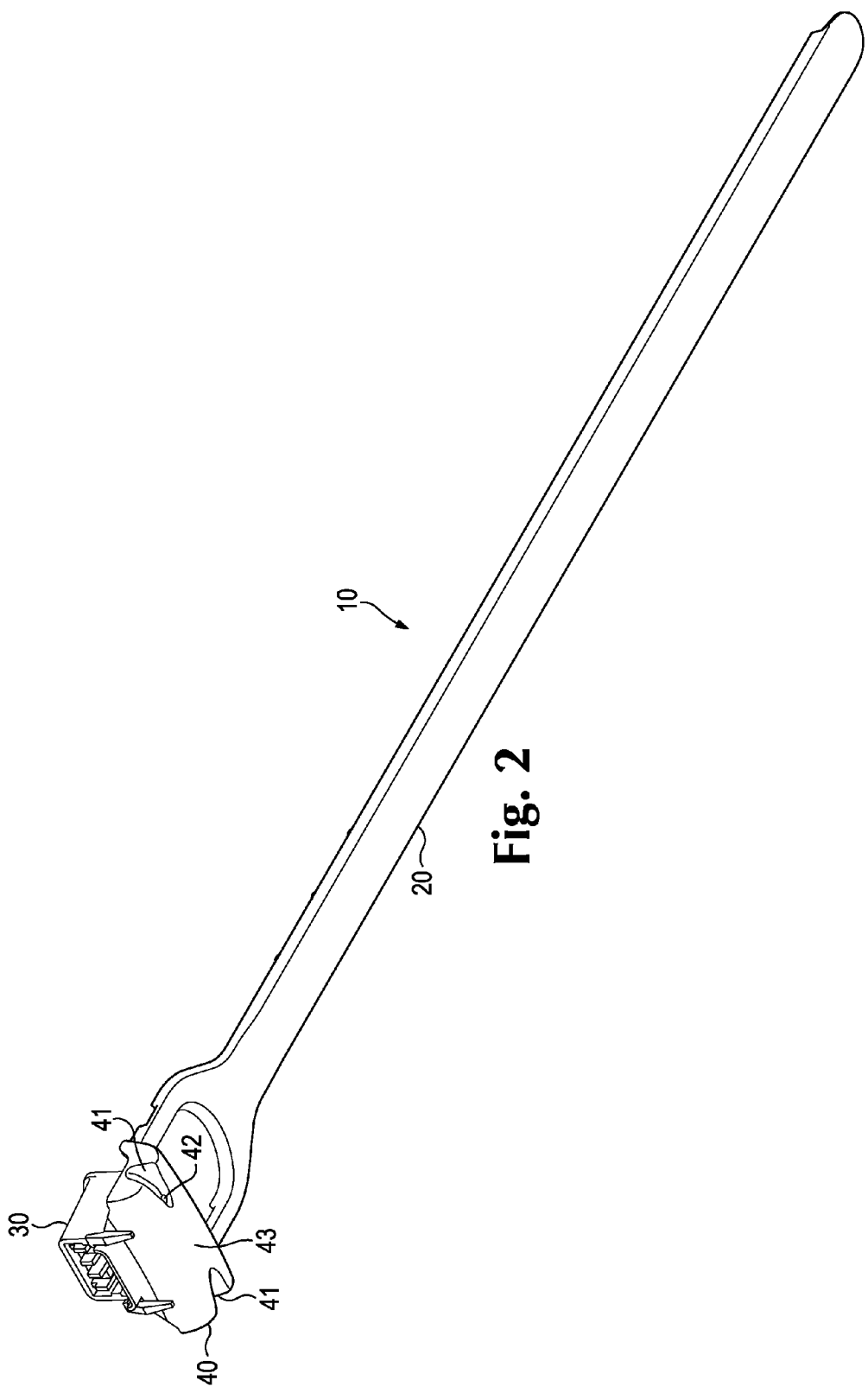

ADJUSTABLE RATCHETING VASCULAR COMPRESSION DEVICE AND METHOD OF USE

This non-provisional utility patent application claims benefit of Provisional Patent Application 61/854,674, which has a filing date of Apr. 29, 2013.

FIELD OF THE INVENTION

The present invention generally relates to devices for occluding and partially occluding blood flow through a blood vessel. More particularly, the invention relates to an apparatus for reducing or stopping blood flow in a blood vessel by means of adjustably applying external compression to the body surface generally overlying said blood vessel.

BACKGROUND OF THE INVENTION

Several devices have been utilized to externally compress blood vessels in various parts of the body for the purpose of reducing or stopping the flow of blood through said vessels. A tourniquet is a simple device used around a limb which, when tightened, reduces or stops arterial blood flow to the distal portions of the limb thereby minimizing hemorrhaging from wounds or punctures in the vessels. For medical procedures, tourniquet-type devices have been specifically designed to prevent bleeding through a cannulation or needle puncture in a vessel in a patient's forearm. U.S. Pat. No. 5,269,803 by Geary et al discloses a strap that encircles the forearm with a pressure pad that applies compression over the vessel to prevent bleeding through the puncture. Other devices that include a strap to prevent bleeding through a puncture site include: U.S. Pat. No. 4,182,338 to Stanulis; U.S. Pat. No. 4,005,709 by Laerdal; U.S. Pat. No. 3,954,109 by Patel; and U.S. Pat. No. 3,586,001 by Sanderson.

Several devices have improved upon the basic tourniquet by applying pressure to only selected points instead of around the entire circumference of the limb, for example: U.S. Pat. No. 6,647,986 by Korotko et al; U.S. Pat. No. 5,728,120 by Shani et al; U.S. Pat. No. 5,601,597 by Arrowood et al; U.S. Pat. No. 5,569,297 by Makower et al; U.S. Pat. No. 5,295,996 by Blair; U.S. Pat. No. 5,234,459 by Lee; U.S. Pat. No. 4,760,846 by Kelly et al; U.S. Pat. No. 4,557,262 by Snow; U.S. Pat. No. 3,570,496 by Sachs; U.S. Pat. No. 2,271,927 by Saighman; and U.S. Pat. No. 1,473,041 by Henderson; and U.S. patent application Ser. No. 12/737,087 by Benz. Each of these devices includes a strap for encircling a patient's limb, and pressure pads or similar devices to apply compression to stop the blood flow through the target vessels in the limb. A device called the TR Band marketed by Terumo, as described in U.S. Pat. No. 7,498,477 by Wada, utilizes a wrist-encircling tourniquet-type strap that applies compression by means of an inflatable bladder.

Other devices are known to the inventors, which, although they do not take the form of a tourniquet or derivative device, help achieve hemostasis in blood vessels. Examples include: U.S. Pat. No. 5,304,186 by Semler, et al; U.S. Pat. No. 4,742,825 by Freund et al; U.S. Pat. No. 4,572,182 by Royse; U.S. Pat. No. 4,233,980 by McRae et al; U.S. Pat. No. 3,779,249 by Semler. These disclose mechanical or pneumatic means of applying compression over a blood vessel for the purpose of allowing a clot to form, thereby enabling hemostasis and corollary cessation of bleeding. Features noted in this art are: i) the use of clamping or inflatable bladder mechanisms to apply compression to the body surface overlying a target blood vessel and not all vessels in or leading to the extremity, and ii) the incorporation of features to gradually reduce compression and permit direct visual observation of a surface wound or puncture site leading to the target vessel close to the point of compression.

Additional patents disclose straps that are used in combination with pressure pads for therapeutic purposes other than occluding the flow of blood: U.S. Pat. No. 5,372,575 by Sebastian; U.S. Pat. No. 5,312,350 by Jacobs; U.S. Pat. No. 5,135,473 by Epler et al.; U.S. Pat. No. 5,078,728 by Giarratano; U.S. Pat. No. 4,590,939 by Sakowski; U.S. Pat. No. 4,479,495 by Isaacson; U.S. Pat. No. 4,323,232 by Terpening; U.S. Pat. No. 4,308,861 by Kelly; U.S. Pat. No. 4,243,028 by Puyana; and U.S. Pat. No. 519,894 by Schutz et al.

The prior art teaches that compression applied externally, i.e. on the body surface and over a target blood vessel slows the blood flow such that a clot can form so that normal hemostasis may occur. The prior art further teaches the value of: i) enabling visual access to the puncture or wound site on the body surface, and ii) providing preferential compression over a target vessel, so that arterial flow to or venous return from an extremity, for example a hand, are important attributes of a device having the purpose of achieving hemostasis following cannulation.

One requirement, well-known to clinical practitioners, which arises following medical procedures involving an arterial puncture, for example, radial artery catheterization, is the necessity to gradually release compression over the vessel to gradually increase blood flow while not disturbing the clot formed during the hemostasis process. Devices used for hemostasis, for example, as described by Semler, provide a means of gradually reducing compression. While there are many references that disclose the broad concept of using a strap with a pressure pad to stop the flow of blood through an arterial puncture wound located on the arm or wrist, none of these devices provides a convenient, low-cost, user-controlled, easily-adjustable means of: i) rapidly applying compression to a blood vessel while the cannula is removed, and ii) adjusting the amount of compression being applied to the point of compression in consistent, fine increments without releasing the fastening mechanism of the apparatus so as to avoid the risk of a bleeding complication due to a sudden unexpected absence of compression, and iii) quickly releasing compression and removing the device from the patient, and iv) integrating the adjustment and fastening means to enhance ease of use, and v) enabling distal blood flow through adjacent blood vessels, for example, distal blood flow through the ulnar artery and venous return from the hand. Although Wada describes an adjustable device, it lacks an integrated means of securing, adjusting and quickly releasing the device within a single structure of the device. Although Benz describes an adjustable device, it does not provide a low cost of manufacture due to its multiple components.

In addition, as initially described by Samir Pancholy, MD in the PROPHET Study of 2007 (Pancholy et al, Catheter Cardiovasc Interv. 2008 Sep. 1; 72(3):335-40. doi: 10.1002/ccd.21639), continued perfusion through the radial artery during the period in which external compression is applied for the purpose of achieving hemostasis at the arteriotomy and puncture site is required in order to reduce the incidence of chronic radial artery occlusion, a not-uncommon complication of radial access. He coined the term, "patent hemostasis" to refer to patency of the radial artery during the hemostasis period and shows that adjusting compression to permit such patent hemostasis helps to avoid chronic radial artery occlusion. Therefore, a need exists for a low-cost, easily adjustable, secure vascular compression device.

SUMMARY OF THE INVENTION

The present invention generally relates to devices for use following cannulation procedures performed on blood vessels in a limb of a patient, for example, during or after radial artery catheterization procedures, or during or after a hemodialysis session, or during or after withdrawal of a cannula from a vein or artery in a patient's arm or other extremity. More particularly, the present invention describes an adjustable vascular compression device which applies compression on a patient's body surface overlying a blood vessel thereby constricting said vessel, for the purpose of reducing or stopping blood flow at that point of compression, for example, generally over the area of a radial artery puncture site, to permit hemostasis to occur at the site by reducing or eliminating blood flow generally at the point of compression. Alternatively the compression may also be applied at a point proximal and/or distal to the puncture site. Further, such compression may be adjusted by the user so as to enable patency in the compressed blood vessel while such hemostasis occurs, i.e. patent hemostasis. Thus, the present invention provides utility in assisting with hemostasis following medical cannulation procedures on the limbs of a patient, for example, in: radial artery catheterization procedures for interventional cardiology, diagnostic cardiology and radiology; surgery; other cardiac procedures including electrophysiology; kidney dialysis; and, withdrawal of catheters, wires or other cannulae from a patient's blood vessels for other medical applications.

The compression device of the present invention has features that permit sufficient adjustable compression to be applied to a target blood vessel to achieve hemostasis while, at the discretion of the user deploying the device on a patient, also maintaining blood flow through the target vessel or other vessels in the limb. For example, the device may be used to partially or fully occlude blood flow through a radial artery while under compression, with adjustments by the user to gradually increase flow as hemostasis occurs, while simultaneously permitting distal arterial blood flow through the ulnar artery and venous return from the hand. In addition, the device further provides: i) a securement means for quickly fastening the device around the patient's wrist and providing compression over the artery, ii) an adjustment means for the user to adjust the compression in small increments without releasing the securement, and iii) a release means further enabling rapid release of compression and removal from the wrist. Notably these securement, adjustment and rapid release means operate by similar actions performed using the same structures of the device. More particularly, the device may be quickly secured and tightened as a cannula is removed to provide compression over the cannulated artery, and subsequently such compression may be tightened or loosened in small increments at the user's discretion without releasing the primary means by which the device is secured. By means of said tightening or loosening, the device enables the operator to apply patent hemostasis.

Preferably, the apparatus is formed of materials that may be simply, inexpensively, and quickly assembled, packaged and pre-sterilized for single-use or multiple-use applications. Alternatively, the device may be provided in partially assembled or non-sterilized form.

In view of the above, an object of the adjustable ratcheting vascular compression device of the present invention is to provide a low-cost apparatus that provides external compression, i.e. onto a body surface, which in turn compresses an underlying target blood vessel for the purpose of slowing or stopping blood flow to assist in achieving hemostasis of a puncture or wound.

Another object of the present invention is to enable the device to be rapidly applied and fastened to the patient and, following use, rapidly removed from the patient.

Another object of the present invention is to enable an operator operating the device to make consistent, fine adjustments in the amount of external compression applied to the vessel following device deployment without releasing the fastening mechanism, one purpose of which is to enable adjustment to permit user-controlled patency of the vessel (i.e. the extent of flow therethrough) during compression, thereby enabling patent hemostasis.

Another object of the present invention is to provide external compression of a target blood vessel while permitting generally unimpeded flow of blood in other adjacent blood vessels, for example, limiting or stopping blood flow in the radial artery while permitting patent flow through the ulnar artery to the hand and venous return from the hand.

Another object of the present invention is to provide an operator with visual access to the area of the puncture site while the compression device is applied to the patient.

Another more particular object of the present invention is to provide external compression of a target blood vessel, specifically an artery or vein in the arm or wrist, directly over or near to a puncture site on the body surface, which leads to an arteriotomy or venotomy, for the purpose of stopping or slowing distal blood flow.

Another more particular object of the present invention is to provide user-adjustable external compression of a radial artery, following a catheterization or other medical cannulation procedure, such that the vessel under compression retains a degree of patency.

The device of the present invention achieves these and other objects through its inclusion of elements that generally include a strap, a housing, a compression pad and levers with pawls that, interacting together with threads located on the strap, enable integrated securement means, adjustment means and rapid release means. Notably said adjustment means is actuated without necessarily releasing the securement of the device. The device is intended to be adjustably secured around a limb of a patient, for example, an arm, forearm or wrist of a patient, with the compression pad placed generally over a puncture site under compression so as to assist with establishing hemostasis at said puncture site. Though these elements are described and shown as separate elements, it will be understood that they may be composed as a unitary construction, for example a unitary injection-molded part formed of a thermoplastic, or as more than one discrete component requiring assembly.

In a preferred embodiment that is for the purpose of establishing post-catheterization hemostasis at a puncture site and arteriotomy in a radial artery, the device is adjustably secured around a wrist by threading the tip of the strap through the housing. The lever pawls engage with the strap threads to secure it in place around the wrist, with the compression pad placed over the area of the puncture site, thereby applying preferential compression over said area. Once the device is tightened thereby applying compression, the design of the hinges, levers, pawls and strap threads enable incremental movement of the strap through the housing by an operator alternately actuating the levers, such movement for the purpose of loosening compression and limited by the amount of an offset between the two rows of strap threads. Such movement thereby enables incremental adjustment of the compression applied to the puncture site area. By actuating both levers simultaneously, the operator may permit the strap to slide freely through the housing to effect complete disengagement of the strap from the housing, thereby rapidly releasing the device entirely from the wrist. A loop may be further included as part of the device, for the purpose of restraining the tip of the strap during deployment and keeping it generally conformal to the curvature of the wrist around which the device is deployed. Such loop may be slidably attached to the strap, or may be formed as part of the strap.

Other similar applications of the device include post-therapy hemostasis of other vascular punctures, and hemostasis of grafts, fistulae, shunts or other vascular punctures in patients following their hemodialysis treatment. A compression pad of shape differing from that shown in the preferred embodiment may be employed for these applications while remaining within the scope of the invention.

All or part of the apparatus, including the compression pad, may be composed of a material, which may be a plastic or other synthetic material, having anti-microbial properties sufficient to prevent growth of microbes or to kill microbes with which it comes into contact, for example on the skin of a patient on whom the apparatus is deployed. Alternatively, the exterior surfaces of the compression pad or other components of the apparatus may be treated with a process or material having anti-microbial properties. Examples of these processes and materials, which are well-known to those skilled in the art, can include: i) the deposition of silver or organic or inorganic particles onto the surfaces of the components of the apparatus by means of vapor deposition or liquid immersion; or ii) including silver or organic or inorganic particles mixed into the materials from which the components are formed.

It will be understood by those skilled in the art that, although the following drawings and Detailed Description disclose further aspects and advantages of the apparatus and describe preferred embodiments, the present invention is not intended to be limited only to these preferred embodiments. It will be apparent that other changes in form and detail may be made therein without departing from the spirit and scope of the invention as defined in the appended claims.

BRIEF DESCRIPTION OF THE DRAWINGS

FIG. 1A is a top perspective view of an adjustable ratcheting vascular compression device, seen from the proximal end.

FIG. 2 is a bottom perspective view of the device.

DETAILED DESCRIPTION OF THE PREFERRED EMBODIMENTS

Figure 1B:
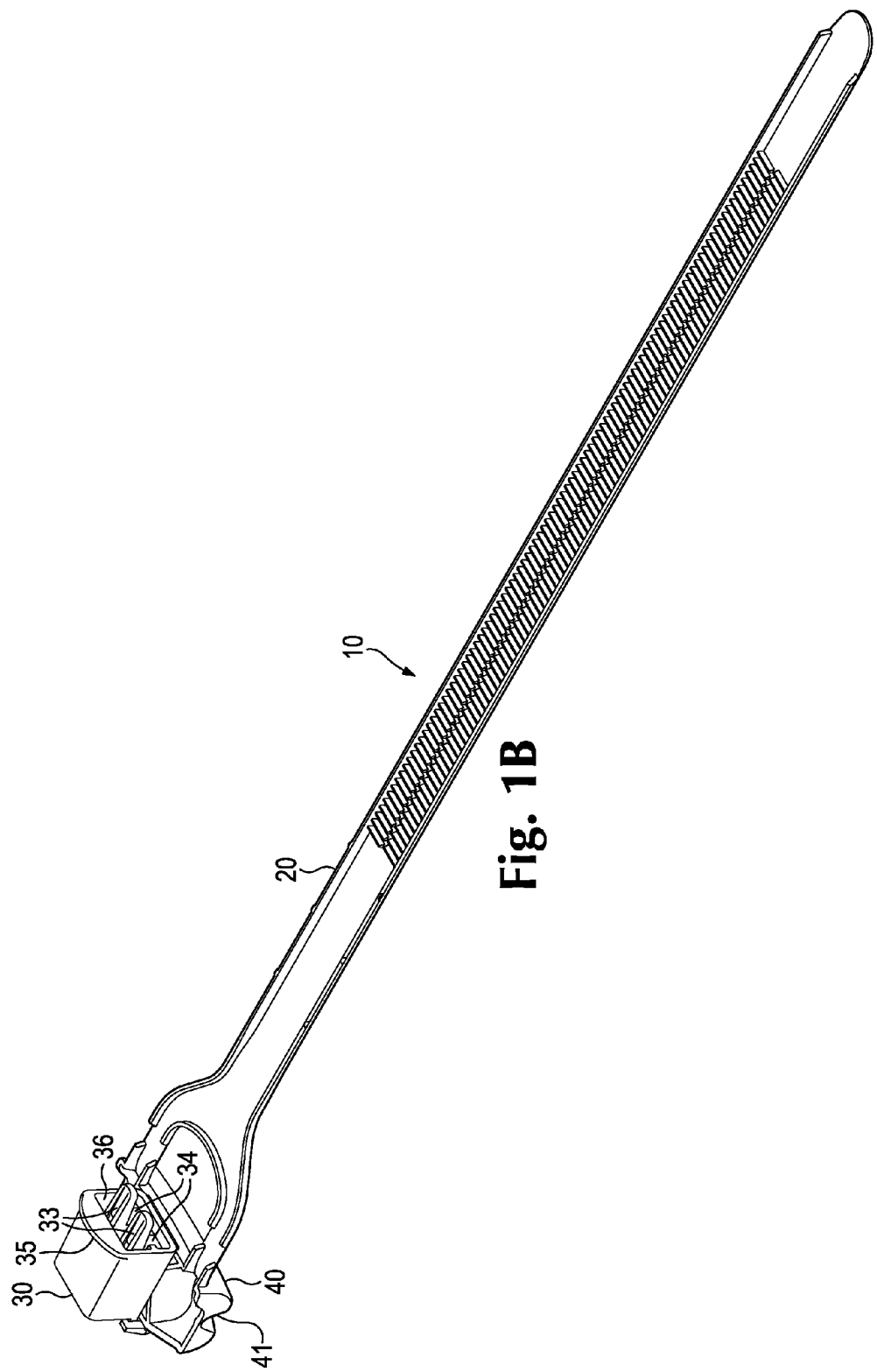
FIG. 1B is another top perspective view of the device, seen from the distal end.

An adjustable ratcheting vascular compression device 10, for use in assisting with post-procedure vascular hemostasis following catheterization or other cannulation, is shown in the drawings and Detailed Description included herein as a preferred embodiment of the present invention. Although the described embodiments are shown as a unitary construction, for example, a single injection-molded plastic part, it will be understood by those skilled in the art that alternative materials and means of construction to achieve the device's objectives and that other changes in form and detail may be employed without deviating from the present invention. In the drawings there are referenced two each of certain components, specifically: for the strap threads 21, the strap thread rows A and B, 21A and 21B respectively; for the levers 33, the levers A and B, 33A and 33B respectively; for the lever pawls 34, the lever pawls A and B, 34A and 34B respectively; for the lever hinges 37, the lever hinges A and B, 37A and 37B respectively. When differentiation between the A and the B components is not necessary, the components shall be referenced only by its number and not the A or B designation.

FIG. 1A shows the compression device 10, which includes a flexible strap 20, a housing 30 and compression pad 40. The strap 20 further includes a distal end 22 and two rows of strap threads 21 formed onto its top surface. The housing 30 further includes two lever hinges 37 (which attach the levers 33, seen in FIG. 1B and not seen in this view, to the housing 30), and housing entry 32. At least the lever hinges 37 are formed of a flexible material, for example, a flexible thermoplastic to permit them to have flexion in the manner of a spring in the vertical axis of travel so that the lever pawls 34 (seen in FIG. 1B, not seen in this view) are forced downward towards the bottom of the interior of the housing 30. The compression pad 40 further includes at least one notch 41 and is formed of a material that has the characteristic of transparency or translucency. The housing 30 has openings at its ends, including the entry 32, permitting passage of the strap 20 therethrough. The device 10 can be formed entirely of a material that has the properties of flexibility and shear strength, since flexibility is needed for it to be twisted, flexed or deflected so that the strap 20 may be fitted around a wrist 100 (seen in FIG. 7, not seen in this view), and since shear strength is needed to enable it to withstand the tension incurred during such deployment. The properties of transparency or translucency, to enable an operator to see through the compression pad 20 is also desirable. Examples of materials embodying such characteristics include, but are not limited to, a polypropylene or other plastic or elastomer or a nylon. Other materials that may be used in at least a portion of the device 10 include woven synthetics or natural materials from plant or animal sources.

FIG. 1B shows the device 10, and its strap 20, housing 30 and compression pad 40. The housing 30 further includes two levers 33 that may be actuated independently, lever pawls 34 on the undersides of levers 33, a thumb rest 35 located on the top side of the housing 30 immediately above the housing exit 36. FIG. 1B further shows a notch 41 located at the bottom and at the end of the compression pad 40. The notch 41 helps the user position the compression pad 40 in the proper location over the area of a puncture site in a blood vessel by providing a guide under which a cannula may slide during its removal from the puncture site. Although the notch 41 is shown at the end of the compression pad 40 in this FIG. 1B, it is within the scope of the invention that it may be located at any other place on the compression pad 40 where it may assist in the proper placement of the pad 40 over a cannula inserted into a vascular puncture site, thereby ensuring that compression is placed over the proper blood vessel, for example the radial artery 102 (seen in FIG. 7, not seen in this view).

FIG. 2 shows the device 10, its strap 20 and housing 30. Below the housing 30 is located a compression pad 40, which during deployment of the device 10 is positioned generally over the vascular puncture site (seen in FIG. 7, not seen in this view) in a patient's limb. The compression pad 40 further includes a bleed hole 42, notches 41, and a compression surface 43 comprising the bottom surface of the compression pad 40. This FIG. 2 shows a notch 41 located at either end of the compression pad 40. Although the bleed hole 42 is shown at the apex of the notch 41 in this FIG. 2, it is within the scope of the invention that it may be located at other places on the compression pad 40. In one embodiment of the invention, the compression pad 40 is dimensioned as follows: the compression surface 43 of the pad 40 has a certain area of between 0.5 and 5.0 square centimeters that may be in a generally rectangular shape, or other shape, and the pad 40 has a certain height of between 0.1 and 2.0 centimeters. The shape of the pad 40 shown has a width that is less than the length however, those of skill in the art will appreciate that alternative dimensions are contemplated as being within the spirit and scope of the invention.

The compression surface 43 may be formed as a unitary part of the compression pad 40, or alternatively as a separate element, e.g. a material expanse that is attached to the compression pad 40. The generally convex shape of the bottom compression surface 43 also helps make deployment more comfortable for the patient by avoiding hard edges of the compression pad 40. It further focuses compression at the center point of the surface 43 as well as providing a long surface for compressing the target blood vessel over, proximal and distal to the arteriotomy. This provides some placement error margin, which may be needed since the arteriotomy, though close to the puncture site, is not directly under it and cannot be directly seen. The compression pad 40 also provides more skin surface coverage as compression increases since it will "sink" into the tissue, since muscle and fat tissue are generally compliant. The notch 41 enables better positioning of the pad along the longitudinal axis of the target blood vessel, e.g. the radial artery 102 (seen in FIG. 7, not seen in this view), since the cannula protruding from its vascular puncture site will fit under the notch 41, thus guiding the user to properly place the pad directly over the target blood vessel and not off to one side. Further the bleed hole 42 serves as another landmark to guide placement, since the user may be instructed to position the compression pad 40 during deployment with the bleed hole 42 positioned over or near the puncture site. Because of the height of the compression pad 40, it applies the compression preferentially to the skin surface it covers, i.e. leaving the areas of skin surface adjacent to it uncompressed.

Those of skill in the art also will appreciate that alternative configurations, shapes, contours, and radii of curvature of features of the compression pad 40 are contemplated as being within the spirit and scope of the invention and that compression surface 43 can be rigid or yieldable, i.e. somewhat compressible or malleable. For example, it can be formed to have a compliant skin contacting surface that 'gives' slightly when pressed against a person's skin, or it can be covered by a material that is so characterized, thereby further increasing the comfort to the patient during use of the invented apparatus. The compression surface 43 is placed generally over the puncture site 106 of, for example, radial artery 102 so as to reduce or halt blood flow 108 (seen in FIG. 8, not seen in this FIG. 2) by partially or completely occluding the vessel to permit a clot to form at the arteriotomy and puncture site 106 during deployment of the device 10.

A concavity may optionally be included within compression surface 43 for the purpose of attaching, either permanently or removably, a separate component to the compression pad 40. For example, a piece of medical gauze, a sponge, a pad, a hemostatic material, or another object can be removably or permanently attached in said concavity, for example by using an adhesive, to assist in compressing the area around puncture site 106. Such materials can be for the purpose of providing cushioning, for comfort, or for assisting with the compression of the target blood vessel, or for otherwise assisting with the medication or hemostasis of the puncture site 106. For example, a gauze bandage may be used for post-dialysis needle site hemostasis, while a pad 40 having an elongate shape and a hemostatic patch, or no additional materials, may be employed for a post-catheterization hemostasis of a radial artery puncture. The concavity can assume alternative forms including a trough-like concavity extending from side to side, or a pocket or depression generally within a central lower surface of the compression pad 40. The concavity can be of a regular shape, e.g. a trough of generally semicircular or parabolic cross section as shown or a pocket of generally semispherical or other regular geometric cross section. Alternatively, the concavity can be of an irregular shape to accommodate any object of irregular shape therein.

In a preferred embodiment for post-catheterization compression of the radial artery 102 (seen in FIG. 7, not seen in this view), the height of the compression pad 40 provides preferential compression directly over the puncture site 106 by positioning the strap away from the body surface 104 to avoid compression applied entirely around the forearm or wrist, thereby enabling blood flow through underlying non-target blood vessels, for example, the vessels 101 and 103. In this instance, the bottom compression surface 43 of the compression pad 40 would extend to a level below the bottom surface of the strap 20.

Figure 3:
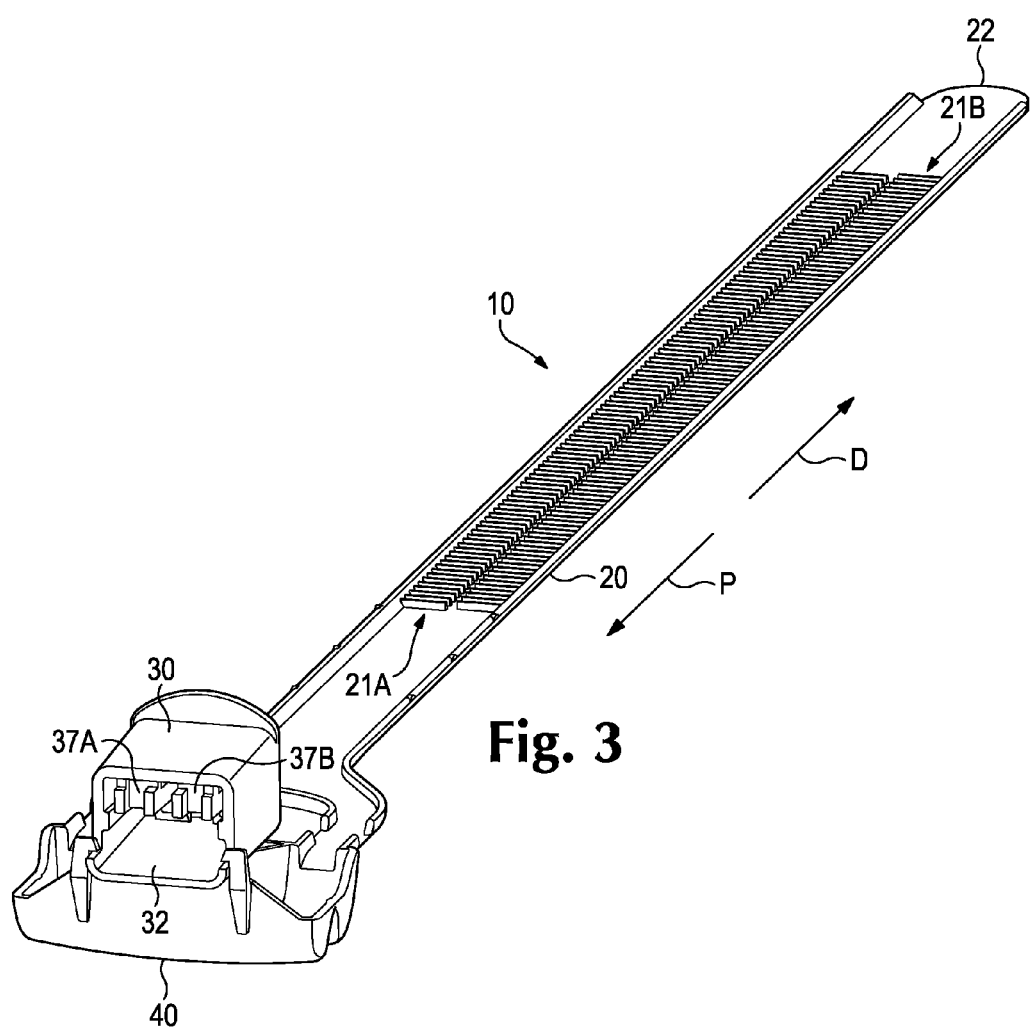
FIG. 3 is another top perspective view of the device, seen from the proximal end.

FIG. 3 shows the device 10, its strap 20, housing 30 and compression pad 40. The distal end 22 of the strap 20 is shown, as is strap thread row A 21A and strap thread row B 21B. The housing 30 includes a housing entry 32, a lever hinge A 37A and lever hinge B 37B. Also indicated are the proximal direction P and distal direction D, both running on the longitudinal axis of strap 20.

Figure 4:
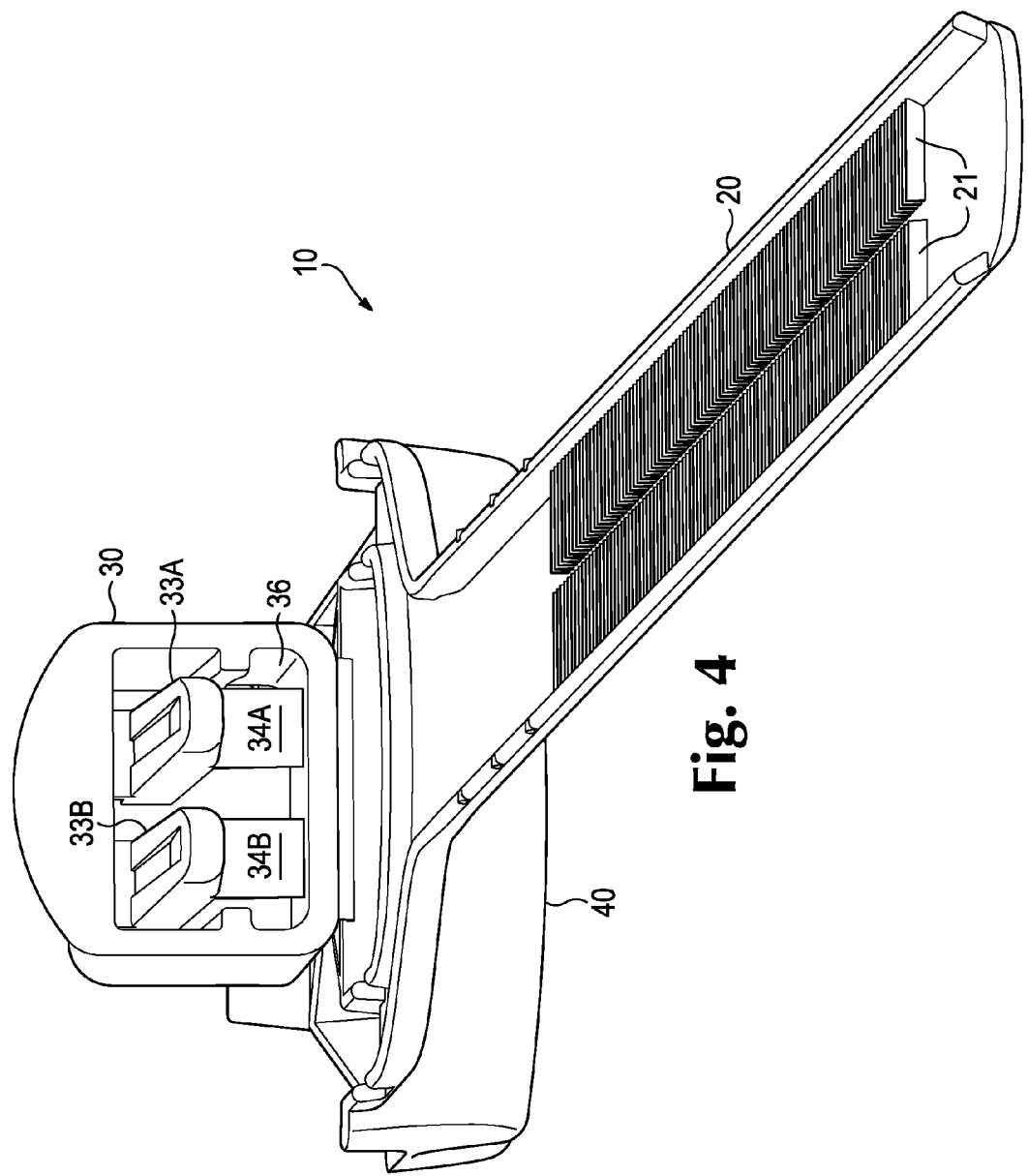
FIG. 4 is another top perspective view of the device, shown from the distal end.

FIG. 4 shows the device 10, its strap 20, housing 30 and compression pad 40. Two rows of strap threads 21 are shown. The housing 30 further includes lever A 33A, lever B 33B, lever pawl A 34A, lever pawl B 34B and housing exit 36. The lever pawls 34A and 34B are located on the undersides of the levers 33A and 33B. The levers 33 are attached to the housing 30 by the hinges 37 (seen in FIG. 1, not seen in this view). Although there are shown two independently actuated levers 33A and 33B and two rows of strap threads 21, it is within the scope of the invention that there may be more than two of each included on the apparatus, as well as of corresponding hinges 37 and pawls 34. This FIG. 4 shows the device 10 as a unitary construction, preferably formed of a flexible material, for example a thermoplastic like a polypropylene or a nylon, thus the relationship of its elements to each other is fixed.

Figure 5A:
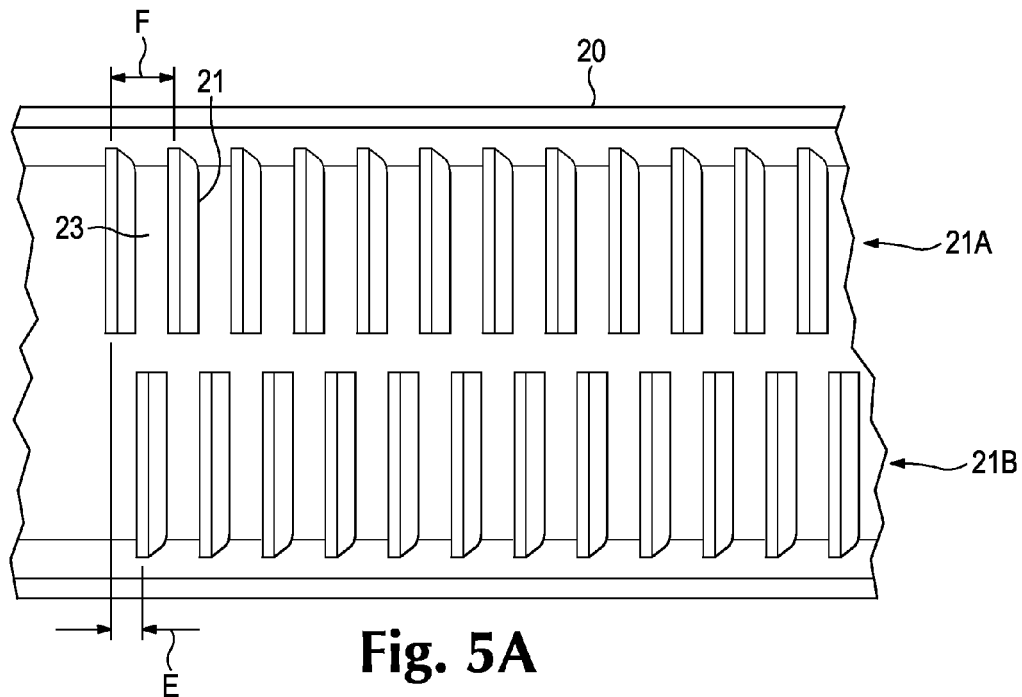
FIG. 5A is a top view of a portion of the strap element of the device.

FIG. 5A shows a portion of the strap 20 with detail presented of the strap thread rows A 21A and B 21B, and further showing detail of a strap thread 21 and gap 23 between the strap threads 21. Strap thread rows A 21A and B 21B are placed adjacently on the top surface of the strap 20 and are slightly offset from one another by an offset distance E so that the strap threads 21 in one row run parallel to but are not aligned with the strap threads 21 in the other row. In this embodiment as shown in FIG. 5A, the centers of the strap threads 21 in one row are placed generally in the center of the gaps 23 between strap threads 21 of the other row. Distance F is the distance between centers of strap threads 21 in a single row, e.g. row A 21A. Offset distance E is the distance between the center of a strap thread 21 in one row, e.g. row A 21A and the center of a strap thread 21 in the other row, e.g. row B 21B, and is the amount of offset between these two rows of strap threads 21. Offset distance E is smaller than distance F, and more particularly in this embodiment is shown as approximately half of distance F. It is within the scope of the invention that these distances E and F may be of differing dimensions than shown in this FIG. 5A. Further, although the offset distance E is shown to be substantially the same for all threads in this embodiment, it is within the scope of the invention that offset distance E may be of differing dimension from one pairing of threads to the next.

Figure 5B:
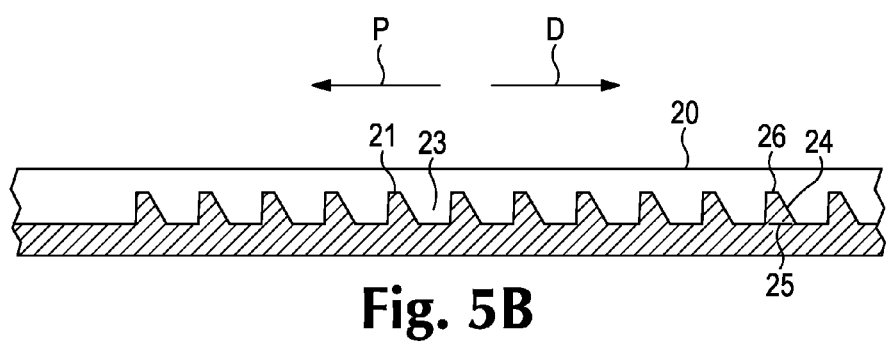
FIG. 5B is a side section view of the strap with parts removed for clarity.

FIG. 5B shows a portion of a single strap thread 21 row, located on the top surface of the strap 20. Also indicated are the proximal direction P and distal direction D, both running on the longitudinal axis of strap 20. Detail is shown of a strap thread 21 and gap 23. The proximal side of the strap thread 21 is generally perpendicular to the top surface of the strap 20, the top of the strap thread 21 is generally flat, and the distal side of the strap thread 21 is sloped at an angle to the top surface of the strap 20. The strap threads 21 are all of uniform but asymmetrical shape, with each thread 21 having a moderate slope on one side, in this view on the distal side, and a steeper or vertical slope on the opposite side, in this view on the proximal side. More particularly, the strap thread 21 has a profile that is shaped generally as a right triangle with its hypotenuse 24 located on its distal side, a base 25 attaching it to the top surface of the strap 20, and a truncated end 26 at its top. It is within the scope of the invention that the shapes and relative dimensions of these strap threads 21 and the gaps 23 may differ from what is shown in this FIG. 5B while still performing their function as described elsewhere in this specification.

Figure 6A:
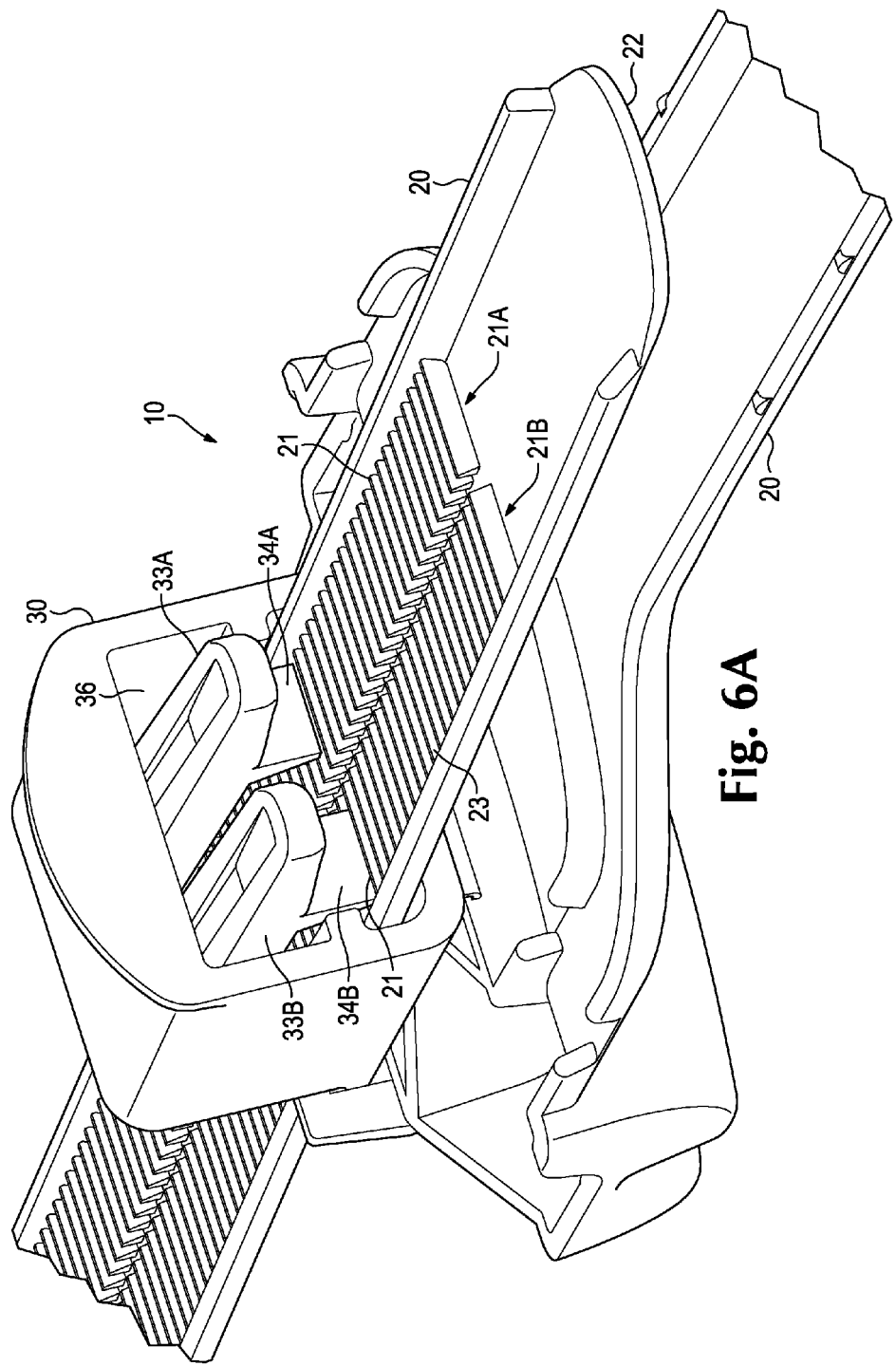
FIG. 6A is a top perspective view of the device with strap inserted into the housing, seen from the distal end.

FIG. 6A shows a portion of the device 10 with distal end 22 of the strap 20 pushed through the housing 30 such that it emerges from the housing exit 36. Levers 33A and 33B are shown, on the undersides of which are lever pawls 34A and 34B respectively, which are shown engaging with the strap threads 21 and gaps 23. While the bottom edge of lever pawl A 34A rests atop strap thread 21 in strap thread row 21A, the bottom edge of lever pawl B 34B rests in the gap 23 between strap threads 21 in strap thread row B 21B because of the offset E (seen in FIG. 5A, not seen in this view) between strap thread row A 21A and strap thread row B 21B. Because of the downward force of the spring action applied to the lever pawls 34 through the levers 33 from the hinges 37 (seen in FIG. 1, not seen in this view), the bottom edges of lever pawls 34 are forced towards the bottom of the interior of the housing 30, thus forcibly contacting the top surface of the strap 20, more particularly the bottom of a gap 23 or the top of a strap thread 21. The structures of the lever pawls 34, the strap threads 21, and gap 23 and the engagement of these structures during operation of the device 10, as described in the foregoing, is thusly enabled by the spring action of the lever hinges 37 so as to enable both a fastening and compression adjustment means through actions performed by an operator using these structures. In this embodiment the lengths of lever A 33A and lever B 33B are the same although it is within the scope of the invention that the lengths of the levers 33 may be different.

Figure 6B:
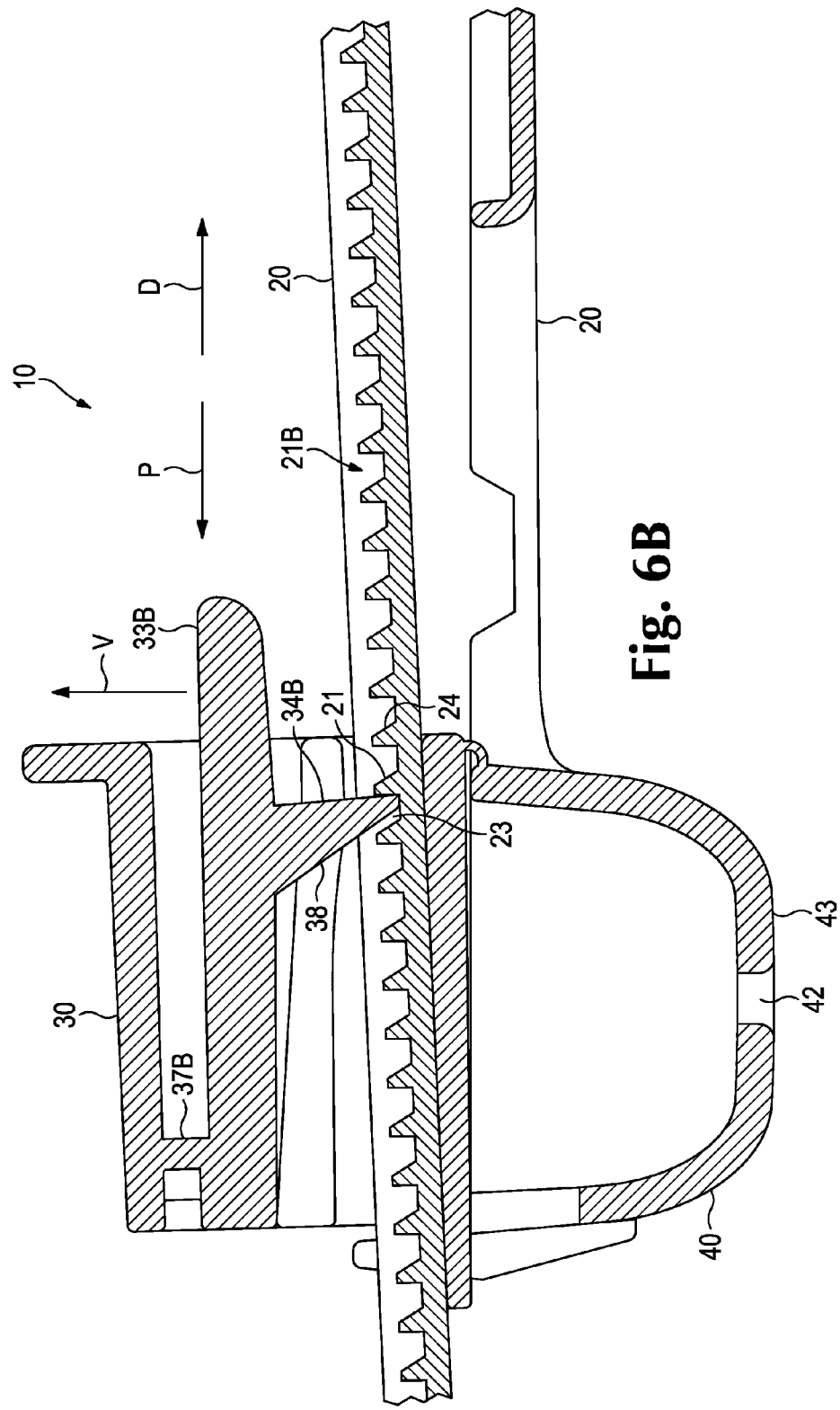
FIG. 6B is a side view of the housing with strap inserted, with parts removed for clarity, showing a lever pawl interacting with strap threads.

FIG. 6B shows a view with parts removed of a portion of the device 10 to show the engagement of the lever pawl B 34B with gap 23 and strap thread 21 in strap thread row B 21B while the strap 20 is inserted through the housing 30. Also indicated are the proximal direction P and distal direction D, both running on the longitudinal axis of strap 20. Movement of the lever pawl B 34B, is initiated by a force exerted in the upward vertical direction V onto the distal tip of lever B 33B, such vertical movement permitted by the spring action of the lever hinge B 37B. While lever pawl B 34B is in the position shown, lever pawl A 34A (not shown in FIG. 6B) is in the position shown in FIG. 6A, i.e. resting atop strap thread 21 in strap thread row A 21A. Also shown in FIG. 6B is the bleed hole 42, extending entirely through the compression surface 43 on the bottom of compression pad 40. The bleed hole may not necessarily extend through the compression surface 43.

In this FIG. 6B side view, the pawl 34B, at an end of the lever 33B that is attached to the housing 30 by hinge 37B, has a shape similar to a right triangle, with its hypotenuse 38 located on its proximal side, and base attaching it to the lever 33B. The hypotenuse 38 and 24 sides of the pawl 34B and the strap thread 21 thus engage with each other when the strap 20 is pulled in the distal direction D, enabling its slidable movement through the housing 30. The vertical sides of both the strap thread 21 and pawl 34 also face each other when the engaging strap thread 21 is distal to the pawl 34, thus preventing movement of the strap 20 in the proximal direction P unless the lever 33 is lifted in vertical direction V, thereby disengaging the pawl 34 from the strap threads 21.

Figure 7:
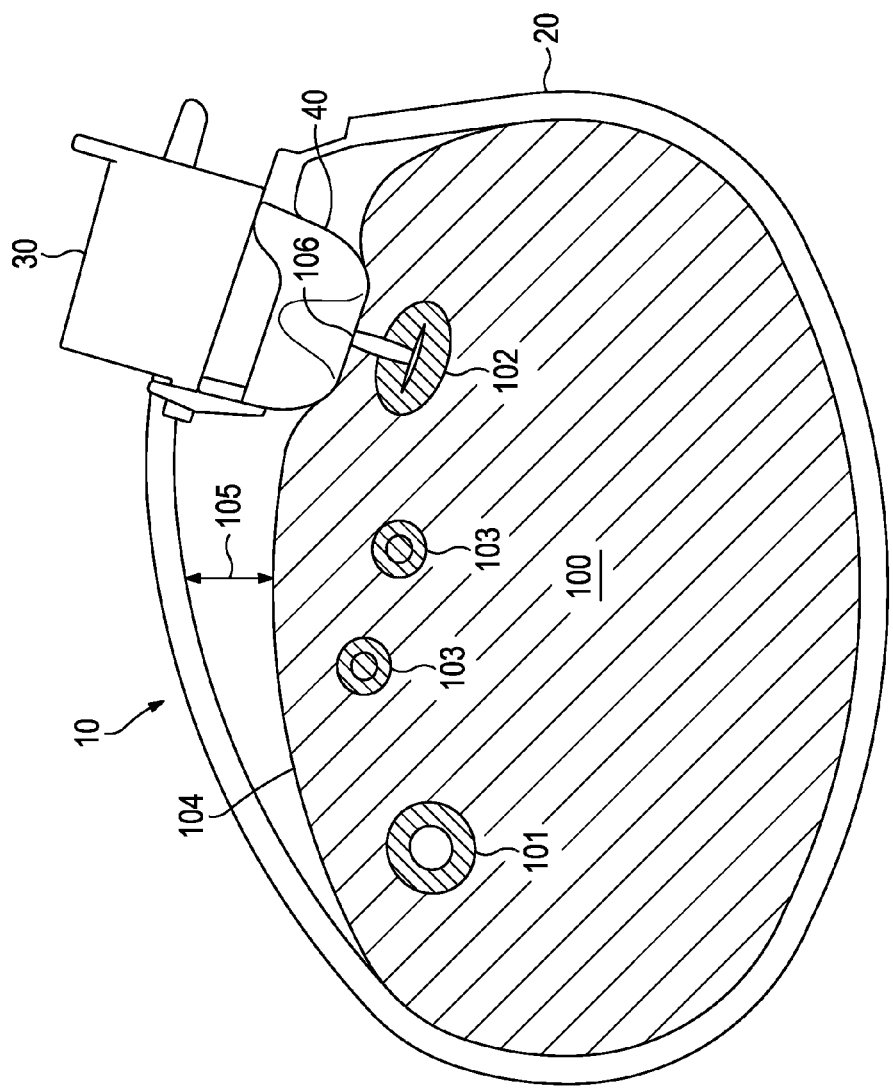
FIG. 7 is a cross-sectional end view of a wrist with the device attached.

FIG. 7 shows application of the device 10 onto a wrist 100 for the purpose of occluding a blood vessel, in this case a radial artery 102, while keeping the ulnar artery 101 and veins 103 "patent" (i.e. permitting blood flow 108, seen in FIG. 8 and not seen in this view, therethrough), by means of the standoff space 105 created between the strap 20 and the surface of the wrist 104, such standoff space 105 being correlated to the height of the compression pad 40, located under the housing 30, the compression pad 40 being placed generally over the puncture site 106.

Figure 8:
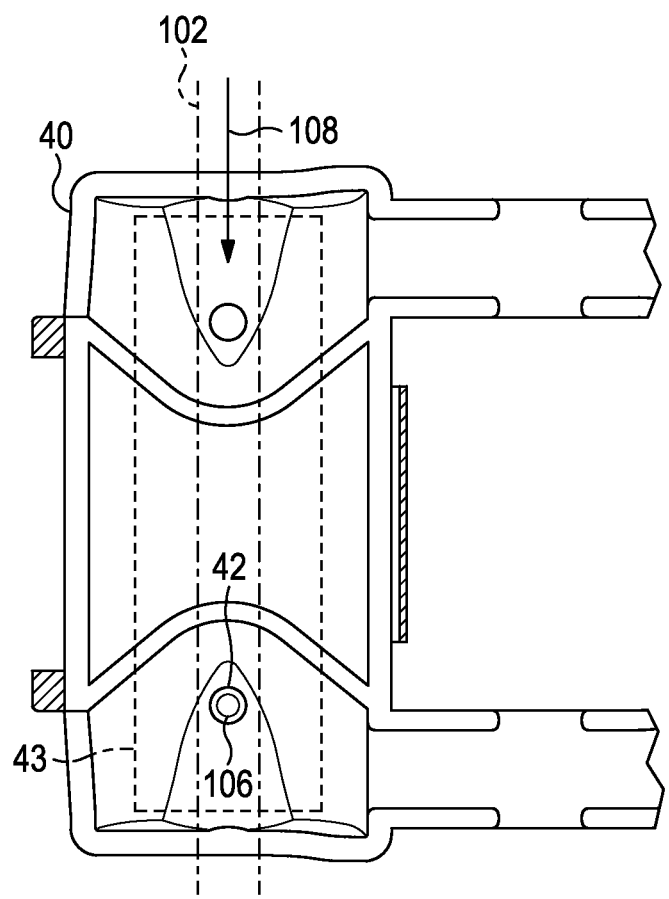
FIG. 8 is a fragmentary top view of the compression pad placed over a puncture site, with parts removed for clarity.

FIG. 8 shows the compression pad 40 in position directly over the radial artery 102 and puncture site 106, with its compression surface 43 overlying the radial artery 102 in its longitudinal axis. The bleed hole 42 is positioned generally over the area of puncture site 106, in this case directly over it, to partially or fully occlude the blood flow 108 during deployment. However, it is within the scope of the invention that the compression pad 40 may be otherwise placed in the area of the puncture site 106. The longitudinal axes of the strap 20 and the compression pad 40 are shown to be perpendicular, although different orientations and configurations are within the scope of the invention.

In its operation, the device 10 generally is secured around a wrist 100 by threading the distal end 22 through the housing entry 32 and pushing it through the housing 30 and pulling it through the housing exit 36. The strap threads 21 engage with the lever pawls 34 for securement. Actuation of the independently actuated levers 33 provide both adjustment and rapid release. More particularly, alternate actuation in direction V of the levers 33, operating as a ratcheting means, enables incremental loosening without release of the device 10, and simultaneous actuation in direction V of the levers 33 enable rapid release. Further, the loosening is made in consistent increments, i.e. the amount of adjustment is the same from one actuation to the next in the embodiments where the offset E is the same between all strap threads 21.

The housing 30 contains at least two levers 33 with pawls 34 attached on their undersides. Each of the levers 33 are connected to housing 30 by hinges 37 at one of their ends, which permit movement of levers 33 in the vertical direction V. The levers 33 are generally of similar shape and equal in dimension, and located side by side such that the distal ends of the levers 33 extend equally outside of the housing exit 36. The pawls 34 are of generally similar shape and dimension. The levers 33 with their attached pawls 34 and hinges 37 are positioned within the housing 30 such that the bottom edge of the pawls 34 rest close to or in contact with the floor of the housing 30 near the housing exit 36, as a result of the spring action of the hinges 37. The hinges 37 act as a spring when the levers 33 are moved upward, for example, when pushed upward by an operator or when a strap 20 is inserted through the housing 30 so as to interfere with the bottom edges of the pawls 34. This spring action results from the flexibility afforded by the material out of which the hinges 37 are fabricated, and the shape and position of the hinge 37 and lever 33 relative to the top and bottom interior surfaces of the housing 30, whereby force is required to move the levers 33 upward from their original position, and when such force is removed the levers 33 and pawls 34 will move back to their original position.

At least two rows of strap threads 21 are placed adjacently on the top surface of the strap 20 and are slightly offset by an offset distance E from one another so that the strap threads 21 in one row run parallel to but are not aligned with the strap threads 21 in the other row(s); for example, with two rows of strap threads 21, each would be offset such that strap threads 21 in one row are placed generally in the center of the interval or gap 23 between straps threads 21 of the other row.

When the distal end 22 is inserted through the housing entry 32 by an operator, it passes out of the housing exit 36, causing the strap 20 and strap threads 21 to engage and interfere with the bottom edges of the pawls 34, the shape and size of the threads 21 and the pawls 34 permitting slidable movement of the strap 20 through the housing 30 as the strap threads' 21 passage causes vertical upward movement of the pawls 34 when the strap 20 is pulled through in the distal direction D. Further, said shapes and sizes prevent movement of the strap 20 in the reverse, or proximal direction P when the strap 20 is not being pulled in the distal direction D, the pawls 34 being kept in place by the spring action of the hinges 37 exerting downward force on the levers 33 and the engagement of the vertical sides of both the strap thread 21 and pawl 34 preventing movement of the strap 20 in the proximal direction P. Such movement in the proximal direction P may be caused by the tension of the strap 20 while it applies compression. Because the action of the pawls 34 with the strap threads 21 permits movement in one direction while preventing movement in the opposite direction, operation of the device 10 has the characteristic of a ratchet. When the strap 20 and strap threads 21 are moving in the distal direction D, the proximal sloped side of pawl 34 easily slides up and over the distal sloped side of thread 21, with the spring action of the hinge 37 pressing down through the lever 33 forcing the bottom edge of the pawl 34 into the gap 23 after it passes the top of each thread 21. When the strap 20 and strap threads 21 move in the opposite or proximal direction P, the vertical distal side of pawl 34 catches against the vertical proximal side of the thread 21, thereby locking it against the thread 21 and preventing any further motion in that proximal direction P. The engagement of the pawls 34 with the strap threads 21 thus provides a securement means, to keep the device 10 in place around a limb, more particularly a wrist 100 of a patient, and at the desired circumference of the strap 20 and amount of compression applied to the puncture site 106.

When the strap 20 is pulled through the housing 30 in distal direction D only the pawls' 34 ratcheting engagement with the strap threads 21 prevents slippage of the strap 20 in the proximal direction P. Securement provided by such engagement preserves the circumference of the strap, the tightness of the strap 20 around the wrist 100 thereby exerting sustained compressive force through the compression pad 40 generally onto the puncture site area 106. The operator, by lifting in the vertical direction V that lever 33 which has its pawl 34 located in the gap 23, may disengage the pawl 34, thereby permitting slippage in the proximal direction P, such vertical motion enabled by the hinge 37 flexing, the upward force exerted by the operator on the lever 33 of necessity being greater than the downward force exerted by the spring action of the hinge 37. Such slippage in the proximal direction P of the strap 20 is limited and is arrested by the other lever 33 and its pawl 34 engaging with a strap thread 21 and gap 23. As a result of the offset of the rows of strap threads 21, the slippage of the strap 20 is limited to offset distance E since the pawl 34 of the lever 33 not being lifted will be forced into gap 23 and will engage and interfere with a strap thread 21. This operation enables the adjustment means, which is accomplished without necessarily having to release the device 10 entirely or risk an adjustment of greater than offset distance E.

For example, when the device 10 is deployed with strap 20 inserted through the housing 30, the bottom edge of pawl A 34A rests atop truncated top end 26 of strap thread 21 in strap thread row 21A while the bottom edge of pawl B 34B rests in the gap 23 in strap thread row 21B, preventing movement of the strap 20 in proximal direction P thereby providing a securement means. Pawl A 34A has no effect on movement of the strap 20 while the vertical side of pawl B 34B, by virtue of its placement in gap 23, presses against the vertical side of a strap thread 21, preventing movement of the strap 20 in the proximal direction P. If the strap 20 were pulled in the distal direction D, it would move since the proximal sloped side of pawl B 34B would ride over the sloped distal side of the strap thread 21. If lever B 33B were lifted, the pawl B 34B would rise out of the gap 23 and disengage with the strap thread 21, permitting movement of the strap 20 in the proximal direction P, such movement limited by the bottom edge of pawl A 34A dropping into the next-most distal gap 23 in strap thread row 21A. Thus, when the levers 33 are actuated alternately the maximum travel of strap 20 with each such actuation is offset distance E. This alternate ratcheting mechanism includes two independently actuated sets of ratchet mechanisms, enables an adjustment means that operates without risking inadvertent release of more compression than desired, and without inadvertently releasing the device 10 in its entirety.

By lifting both levers 33 simultaneously, the bottom edges of both pawls 34 are completely disengaged from both rows of strap threads 21 and the strap 20 is able to slidably move freely through the housing 30. By also moving the strap 20 in the proximal direction P while both levers 33 are being lifted, the strap 20 may be completely withdrawn from the housing 30 and release of the device 10 from the patient is effected, thus enabling a rapid release means.

Thus the pawls 34 of the levers 33 that are attached to the housing 30 by hinges 37 engaging with the threads 21 on the top of the strap 20 comprise a ratcheting apparatus, which, by using similar actions on the same structures provides an adjustment means and a rapid release means integrated in both actions and structures. In particular, lifting one or both levers 33 that are attached to a housing 30 by hinges 37, disengages pawls 34 from strap threads 21 to enable i) slidable movement of the strap 20 for limited incremental movement in the loosening or releasing direction P, or ii) a complete rapid release of device 10, depending on whether one or both levers 33 are lifted. A securement means is also integrated in action and structure since the ratcheting action of the pawls 34, which are attached to the levers 33 in turn attached to a housing 30 by hinges 37, engaging with strap threads 21, enable slidable movement of strap 20 through the housing 30 in a tightening or securing direction, i.e. in direction D, and are simultaneously prevented from releasing, i.e. moving in loosening direction P, by such engagement.

A method of using the device of the present invention includes the following steps:

i) Placing the compression surface 43 on the wrist 100. An operator fits the device 10 around a wrist 100 of a patient and pulls the distal end 22 through the housing 30, fastening it loosely so that the compression pad 40 may be moved to the desired point generally overlying the blood vessel, for example a radial artery 102. The method provides that the device 10 need not necessarily be pulled tight initially, and this first step serves to position and keep in place the compression surface 43 relative to the puncture site 106, in which the cannula or needle is still located. The operator may also further position the compression surface 43 by placing the notch 41 over the cannula and the bleed hole 42 over the puncture site 106.

ii) Securing the device 10 while pulling out the cannula. The operator pulls out the cannula or needle from the puncture site 106 with one hand and presses down on top of the housing 30 to apply compression to slow the blood flow 108 with the other. After discarding the cannula and while continuing to press down onto the housing 30, the operator pulls the distal end 22 until the device 10 is tightly secured around the wrist 100 so as to further slow or stop the blood flow 108 and ensure there is no bleeding from the puncture site 106. Alternatively a second person may pull out the cannula as the operator pulls the distal end 22 with one hand to tighten the device 10 while with their other hand presses down on top of the housing 30.

iii) Adjusting the amount of compression applied to the surface of the wrist 100. The operator, by alternately actuating the levers 33 loosens the device 10 to adjust the amount of compression applied to the surface 104 of the wrist 100 so that the blood vessel, for example, the radial artery 102 retains a degree of patency, i.e. continued blood flow 108 through the vessel 102 during the compression period, while hemostasis occurs at the arteriotomy and puncture site 106. Compression may be further gradually reduced during the period in which hemostasis occurs to help avoid complications.

iv) Releasing the device 10 from the wrist 100. The operator, by lifting both levers 33 simultaneously, frees the strap 20 to enable unrestricted slidable movement and pulls the strap 20 in the proximal direction P through the housing 30 to release the device 10 from the wrist 100 of the patient, thereby rapidly removing the device 10 from the wrist 100 entirely.

It can be readily observed that the present invention is distinctive and novel, standing apart from the devices of the prior art, since none make use of an alternate ratcheting mechanism nor do they integrate securement, adjustment and release means all within a single mechanism. The device 10 therefore provides the advantage of consistent, fine incremental compression adjustment without releasing the compression apparatus and risking a complication of a rebleed. Further, the device 10 achieves its objectives as a low-cost apparatus that provides external compression onto a puncture in a body surface for the purpose of slowing or stopping blood flow to assist in achieving hemostasis of a puncture or wound; it is easily deployed and removed, and because the operator can make consistent fine compression loosening adjustments without releasing the device 10, it thereby helps to achieve patent hemostasis and permit blood flow in blood vessels adjacent the target vessel while providing the operator with visual access to the puncture site during deployment.

It will be understood that the present invention is not limited to the process or detail of construction, fabrication, material, application or method of use described and illustrated herein. Indeed, any suitable variation of fabrication, use, or application is contemplated as an alternative embodiment, and thus is within the spirit and scope of the invention. Accordingly, while the present invention has been shown and described with reference to the foregoing embodiments of the invented apparatus and method of use, it will be apparent to those skilled in the art that other changes in form and detail may be made therein without departing from the spirit and scope of the invention as defined in the claims. In particular, though the FIG. 8 and foregoing description references usage on a radial artery, the application of the invention is more broadly to a blood vessel in a limb of a patient and not restricted only to the radial artery.

It is further intended that any other embodiments of the present invention that result from any changes in application or method of use or operation, configuration, method of manufacture, shape, size, or material, which are not specified within the detailed written description or illustrations contained herein yet would be understood by one skilled in the art, are within the scope of the present invention.

We claim:

1. An adjustable ratcheting vascular compression device deployed onto a patient for partially or completely occluding blood flow in a blood vessel in a limb of the patient by adjustably applying preferential compression to said vessel and, following deployment, enabling loosening in consistent, fine increments without enabling complete release of such compression, the device including:
a housing;
a compression pad located on the underside of the housing;
a flexible strap connected to a side of the housing;
threads placed in at least two rows on the top surface of the strap;

at least two independently manually actuated levers, each having a pawl on its underside for engaging with the threads and attached to the interior of the housing by a hinge, the hinge having flexion in the manner of a spring; wherein centers of the threads in one row are offset from centers of the threads in another row by an offset distance;

wherein only one thread is engaged with only one pawl of the at least two pawls, to prevent slidable movement of the strap through the housing, at any time;

lifting the lever to which is attached the pawl then engaged with the thread, to prevent slidable movement of the strap through the housing, disengages the pawl from the thread to enable such slidable movement, which is limited to the offset distance.

2. The device of claim 1, wherein the compression pad, having a compression surface on its underside, further includes at least one notch at an end in the compression surface.

3. The device of claim 1, wherein at least the hinge is formed of a flexible thermoplastic.

4. The device of claim 1, more particularly being formed as a unitary construction.

5. The device of claim 1, wherein each thread has the profile of a right triangle with a truncated top.

6. An operator-actuated alternate ratcheting mechanism for use in a device that is placed onto a patient for partially or completely occluding blood flow in a blood vessel in a limb of a patient by adjustably applying preferential compression to said vessel, more particularly loosening in consistent, fine increments without enabling complete release of such compression, said ratcheting apparatus comprising the elements of at least:

a housing;

a flexible strap connected to a side of the housing;

threads placed in at least two rows on the top surface of the strap;

at least two independently actuated levers, each having a pawl on its underside for engaging with the threads, attached to the interior of the housing by a hinge, the hinge having flexion in the manner of a spring; wherein centers of the threads in one row are offset from centers of the threads in another row by an offset distance;

wherein only one thread is engaged with only one pawl of the at least two pawls, to prevent slidable movement of the strap through the housing, at any time;

lifting the lever to which is attached the pawl then engaged with the thread, to prevent slidable movement of the strap through the housing, disengages the pawl from the thread to enable such slidable movement, which is limited to the offset distance.

7. The housing of claim 6, further including a compression pad located on its underside that has a compression surface on its underside and at least one notch at an end in the compression surface.

8. The hinge of claim 6, more particularly being formed of a flexible thermoplastic.

9. The ratcheting mechanism of claim 6, more particularly being formed entirely of a flexible thermoplastic in a unitary construction.

10. The threads of claim 6, each more particularly having the profile of a right triangle with a truncated top end.

* * * * *